(12) United States Patent
Tsumaru et al.

(10) Patent No.: US 9,675,234 B2
(45) Date of Patent: Jun. 13, 2017

(54) MEDICAL APPARATUS

(71) Applicant: OLYMPUS CORPORATION, Tokyo (JP)

(72) Inventors: Masayo Tsumaru, Sagamihara (JP); Toshio Nakamura, Hachioji (JP); Tatsuya Furukawa, Hachioji (JP); Koji Yamaya, Hachioji (JP); Seiji Saito, Kodaira (JP); Tetsuhiro Yamada, Hachioji (JP); Kahori Yasunaga, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/015,270

(22) Filed: Feb. 4, 2016

(65) Prior Publication Data
US 2016/0150946 A1    Jun. 2, 2016

Related U.S. Application Data

(63) Continuation of application No. PCT/JP2014/077855, filed on Oct. 20, 2014.

(30) Foreign Application Priority Data

Oct. 31, 2013   (JP) ................................. 2013-227728

(51) Int. Cl.
A61B 1/00       (2006.01)
A61B 1/015      (2006.01)
(Continued)

(52) U.S. Cl.
CPC ...... *A61B 1/00098* (2013.01); *A61B 1/00128* (2013.01); *A61B 1/015* (2013.01);
(Continued)

(58) Field of Classification Search
CPC ..... A61B 1/00098; A61B 1/018; A61B 1/015; A61B 1/00066; A61B 1/00128
See application file for complete search history.

(56) References Cited

U.S. PATENT DOCUMENTS 4,198,959 A  *  4/1980  Otani ................. A61B 1/00098
                                                          600/106
5,674,181 A  *  10/1997 Iida ....................... A61B 1/0008
                                                          600/121

FOREIGN PATENT DOCUMENTS

JP    S58-168301 U    11/1983
JP    H09-238898 A     9/1997
(Continued)

OTHER PUBLICATIONS

English translation of International Preliminary Report on Patentability dated May 12, 2016 together with the Written Opinion received in related International Application No. PCT/JP2014/077855.

(Continued)

*Primary Examiner* — Timothy J Neal
(74) *Attorney, Agent, or Firm* — Scott, Scott, Murphy & Presser, P.C.

(57) ABSTRACT

A sealability acquiring mechanism disposed in a medical apparatus has a raising base unit constituted of a raising base operating mechanism, a raising tube path portion, a guide tube and a raising base. In the raising tube path portion, there is disposed a sealing member that is water-tightly or air-tightly fixed to a wire fixing portion to be connected to a raising wire inserted into an outer peripheral member and the outer peripheral member, a fluid supplied from an opening of the outer peripheral member flows between an inner peripheral surface of a raising tube path and an outer peripheral surface of the sealing member, and the raising (Continued)

base operating mechanism is water-tightly or air-tightly separated from the raising tube path.

10 Claims, 11 Drawing Sheets

(51) Int. Cl.
    *A61B 1/018*     (2006.01)
    *A61B 1/12*     (2006.01)
    *A61B 1/04*     (2006.01)
    *A61B 1/005*     (2006.01)

(52) U.S. Cl.
    CPC .............. *A61B 1/018* (2013.01); *A61B 1/126* (2013.01); *A61B 1/0052* (2013.01); *A61B 1/00066* (2013.01)

(56) References Cited

FOREIGN PATENT DOCUMENTS

| | | |
|---|---|---|
| JP | H10-5174 A | 1/1998 |
| JP | 2000-116598 A | 4/2000 |

OTHER PUBLICATIONS

International Search Report dated Jan. 20, 2015 issued in PCT/JP2014/077855.
Chinese Office Action dated Feb. 28, 2017 in Chinese Patent Application No. 201480052697.5.

* cited by examiner

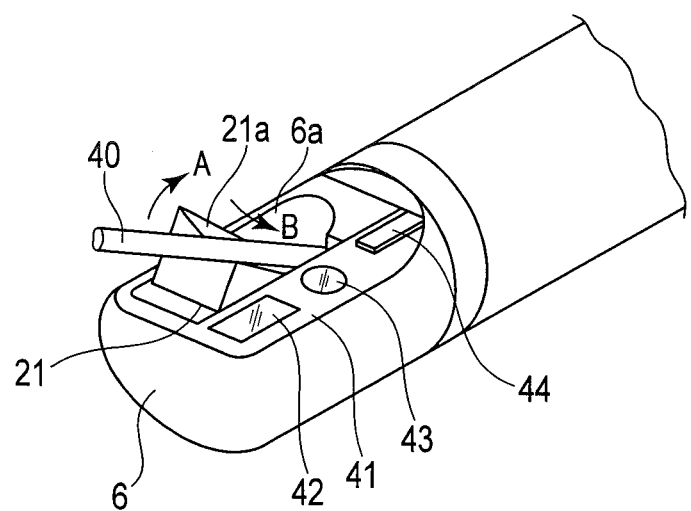
F I G. 3C

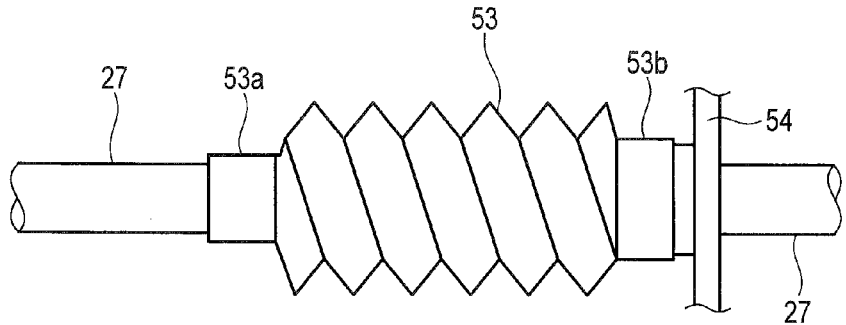
F I G. 7
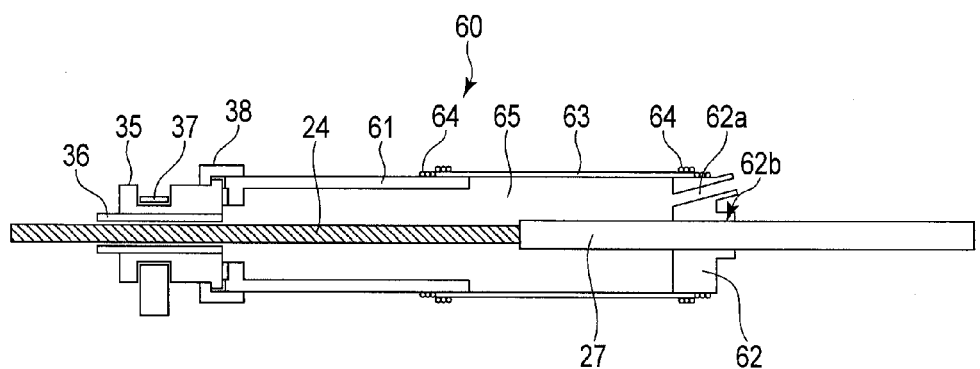
F I G. 8A
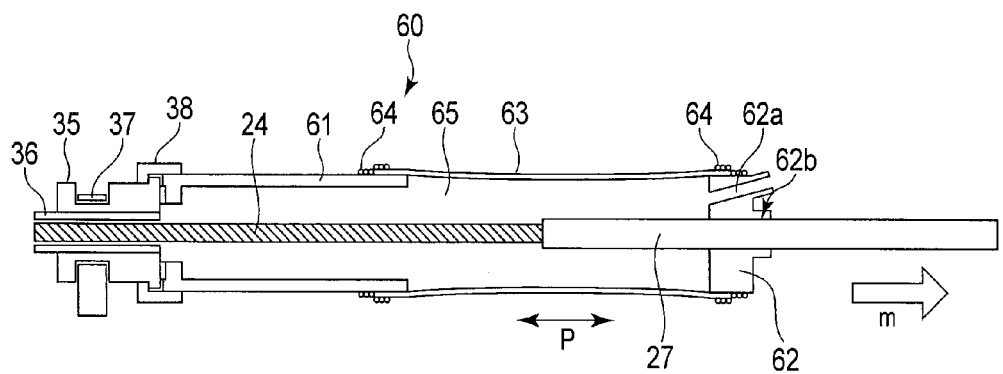
F I G. 8B

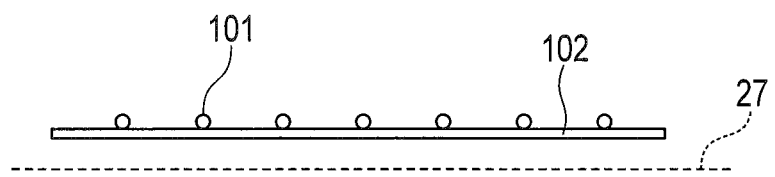
F I G. 12A
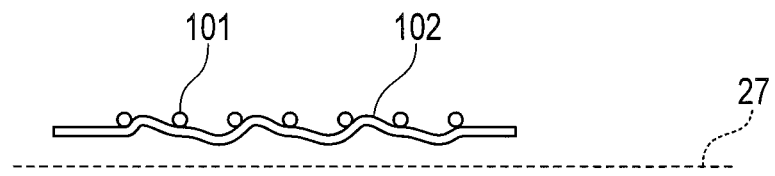
F I G. 12B
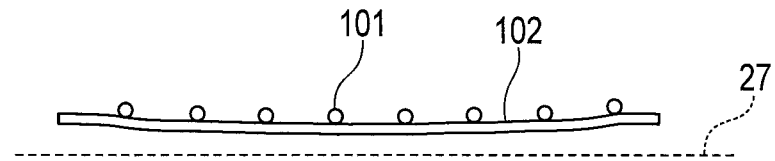
F I G. 12C

MEDICAL APPARATUS

CROSS-REFERENCE TO RELATED APPLICATIONS

This is a Continuation Application of PCT Application No. PCT/JP2014/077855, filed Oct. 20, 2014, which was published under PCT Article 21(2) in Japanese.

This application is based upon and claims the benefit of priority from prior the Japanese Patent Application No. 2013-227728, filed Oct. 31, 2013 the entire contents of which are incorporated herein by references.

BACKGROUND OF THE INVENTION

1. Field of the Invention

The present invention relates to a medical apparatus in which a raising base is disposed on a distal end side of an inserting portion and water tightness and air tightness are imparted to a pulling mechanism of the raising base housed in an operating section.

2. Description of the Related Art

In general, a treatment tool having various functions, e.g., a forceps is inserted into an endoscope main body and extended from an opening opened on a distal end side. For example, a treatment tool raising base is known in which an opening is disposed in a part of a peripheral surface side of a distal end of an endoscope main body, and a treatment tool such as a guide wire extended laterally from the opening is bent in a desirable direction.

The treatment tool raising base is revolved and bent by an operating section disposed on a proximal end side of an endoscope while supporting the guide wire, so that the treatment tool can be directed in the desirable direction of an operator. The operating section is coupled with the treatment tool raising base via a wire or the like inserted into a forceps raising tube path.

A treatment tool raising base portion is inserted and used in a body cavity, and hence after the portion is used, a washing treatment in the forceps raising tube path is performed. Therefore, as suggested in, for example, Jpn. Pat. Appln. KOKAI Publication No. H09-238898, an O-ring made of an elastic material is fitted the wire or a wire stopper to realize a watertight (or airtight) constitution so that a liquid such as a washing liquid does not invade the operating section of the endoscope through the tube path from the opening.

The abovementioned watertight constitution in the forceps raising tube path is realized by the O-ring, and hence, a sliding resistance between the wire and the O-ring increases. That is, the sliding resistance acts in a braking manner to an operation of an operating lever connected to the wire, and hence, the operation of the operating lever becomes heavy, and it is difficult for the operator to adjust an operating force, which becomes one reason why a delicate operation is hard to be performed. In addition, conversely, when the sliding resistance between the wire and the O-ring is decreased, water tightness and air tightness deteriorate, and there is the fear of a situation such as the invasion of the washing liquid into the operating section or the invasion of the liquid into the body cavity during the use.

BRIEF SUMMARY OF THE INVENTION

According to an embodiment of the present invention, there is provided a medical apparatus having: a raising tube path member comprising a revolvable raising base in its distal end portion; a pulling member inserted into a tube path of the raising tube path member to revolve the raising base; a link mechanism connected to the pulling member to impart a pulling force to the pulling member; and a sealing member that is water-tightly or air-tightly fixed to each of the tube path and the pulling member, is deformable in accordance with movement of the pulling member, and water-tightly or air-tightly separates an inner portion of the tube path from the link mechanism.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiment given below, serve to explain the principles of the invention.

FIG. 3C is a view showing an appearance constitution when a raising base of the distal end portion of the inserting portion is raised;

FIG. 7 is a view showing an appearance constitution of a sealing member of a sealability acquiring mechanism according to a third modification of the first embodiment;

FIG. 8A is a cross-sectional view showing a constitution of a raising tube path comprising a sealability acquiring mechanism according to a second embodiment, and a state when a raising base is inverted;

FIG. 8B is a cross-sectional view showing a state when the raising base is raised;

FIG. 12A is a view showing a constitution of a spring guide disposed in a sealing member of a modification according to the second and third embodiments;

FIG. 12B is a view showing a constitution of the spring guide disposed in the sealing member of the modification according to the second and third embodiments; and FIG. 12C is a view showing a constitution of the spring guide disposed in the sealing member of the modification according to the second and third embodiments.

DETAILED DESCRIPTION OF THE PREFERRED EMBODIMENT

Hereinafter, embodiments of the present invention will be described in detail with reference to the drawings.

Figure 1:
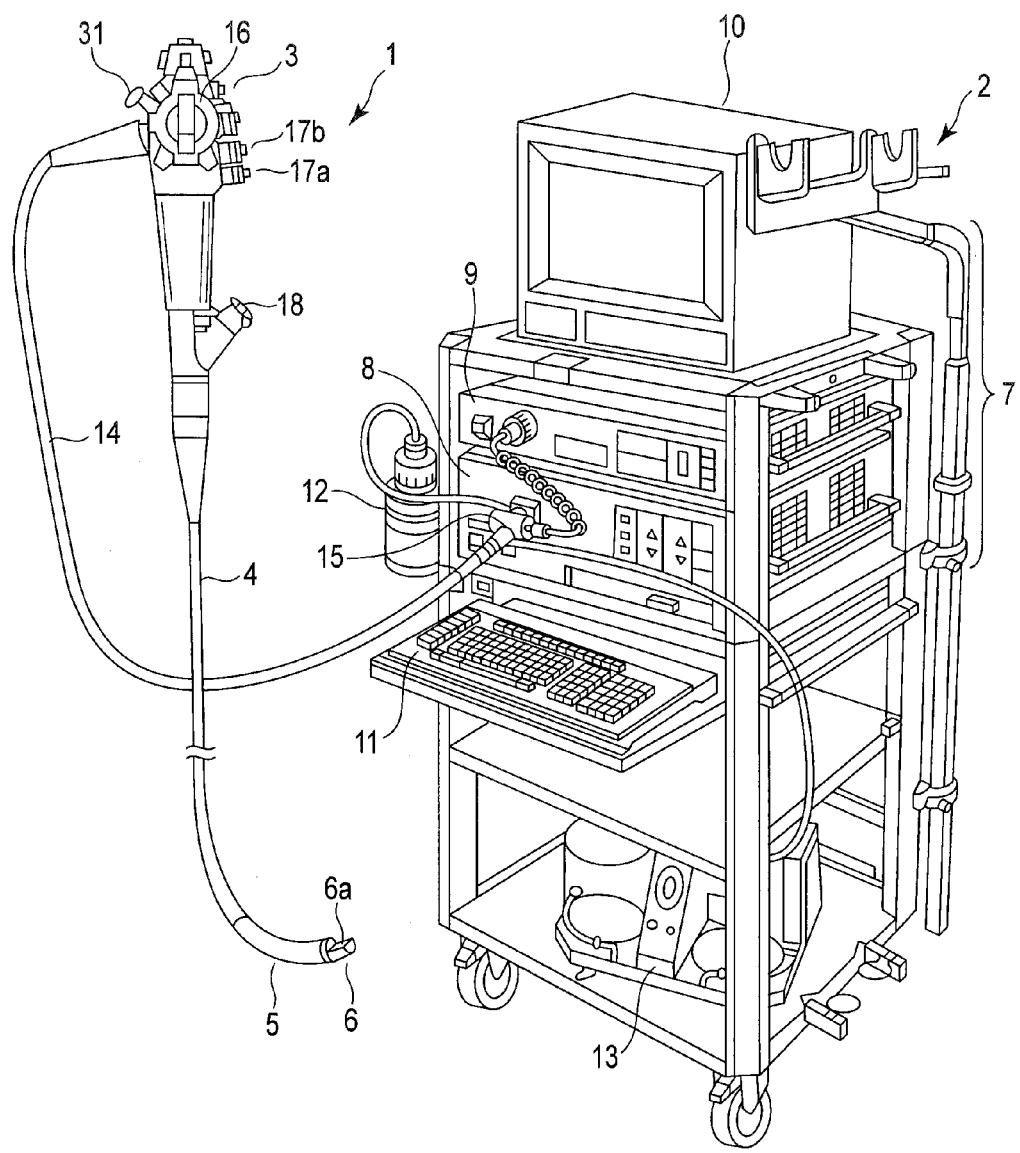
FIG. 1 is a view showing an example of the whole constitution of an endoscope apparatus in which a raising base unit is disposed in an endoscope main body, as a medical apparatus of the present invention.
Figure 2:
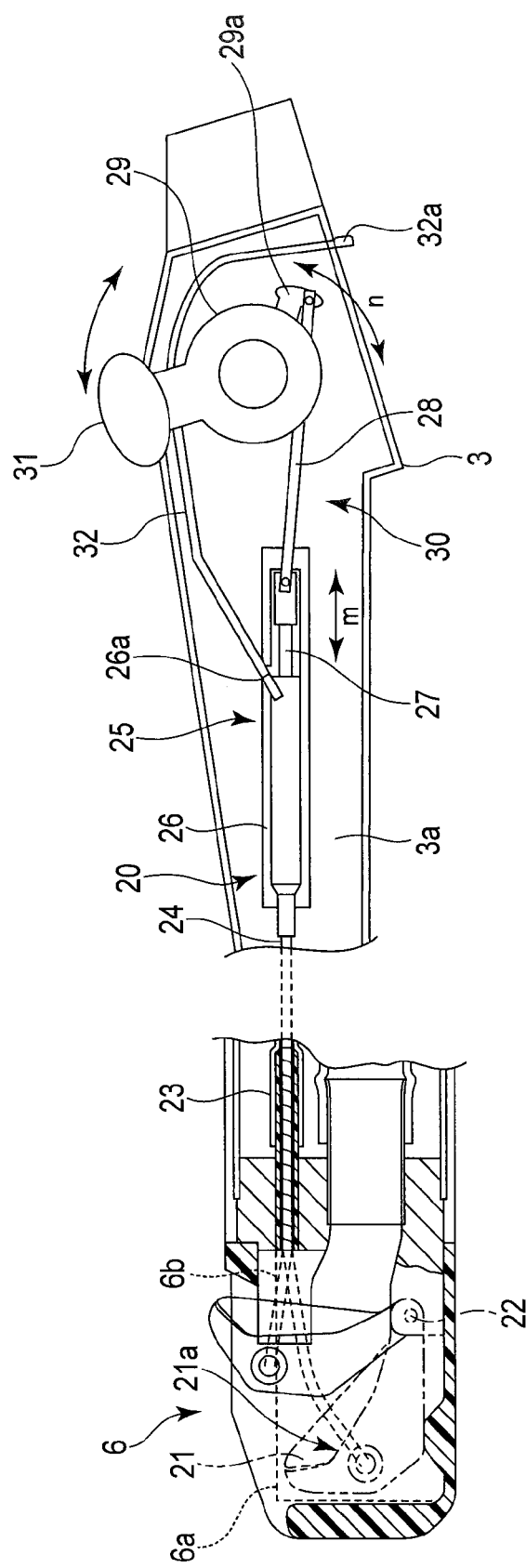
FIG. 2 is a view conceptually showing a constitution of the raising base unit disposed in the endoscope main body.
Figure 3A:
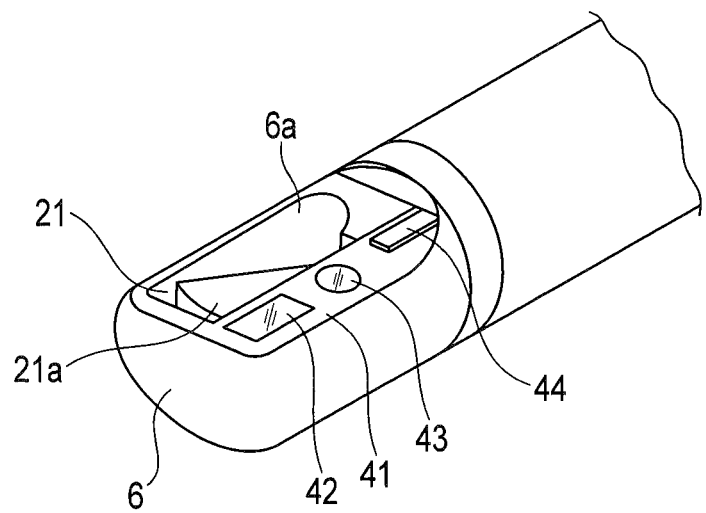
FIG. 3A is a view showing an appearance constitution of a distal end portion of an inserting portion.
Figure 3B:
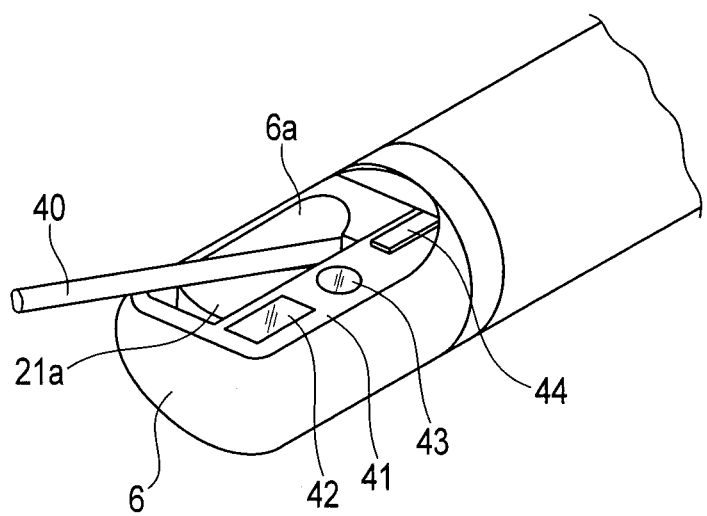
FIG. 3B is a view showing the appearance constitution of the distal end portion of the inserting portion.

FIG. 1 is a view showing an example of the whole constitution of an endoscope apparatus in which a raising base unit is disposed in an endoscope main body, as a medical apparatus of the present invention. FIG. 2 conceptually shows a constitution of the raising base unit disposed in the endoscope main body, FIGS. 3A and 3B show an appearance constitution of a distal end portion of an inserting portion, and FIG. 3C shows an appearance constitution when a raising base of the distal end portion of the inserting portion is raised.

The endoscope apparatus of the present embodiment is roughly constituted of an endoscope main body 1, and an apparatus 7 for an endoscope which is constituted of various external devices mounted on a movable trolley 2. In the following description, a flexible endoscope will be described as an example, but a hard endoscope can similarly be mounted.

The endoscope main body 1 is constituted of an inserting portion (a flexible tube) 4 to be inserted in a body cavity that is an observation object, a bendable portion 5 and an after-mentioned distal end portion 6 which are disposed on a distal end side of the inserting portion 4, and an endoscope operating section 3 disposed on a proximal end side to bend and operate the bendable portion 5. In the following description, a bendable portion 5 side will be referred to as the distal end side, and an operating section 3 side will be referred to as the proximal end side.

The apparatus 7 for the endoscope has a light source device 8 that generates illuminating light with which an observation object region is to be irradiated, a video processor 9 that subjects an imaged video signal to predetermined image processing, a monitor 10 that displays the video signal as an observation image, a keyboard 11 as an inputting section, and the like.

Furthermore, a bottle 12 in which a liquid for use in washing or the like (a washing liquid, e.g., a liquid mainly containing water such as saline) is stored is detachably attached to the trolley 2. In addition, the apparatus 7 for the endoscope includes a supply gas pump unit (not shown). Furthermore, on a shelf of the trolley 2, there is disposed a suction unit 13 that sucks a liquid, a gas, a viscous liquid and the like jetted into the body cavity, from an after-mentioned washing nozzle in the body cavity.

The endoscope main body 1 and the light source device 8 are connected to a connector 15 via a universal cable 14. The universal cable 14 includes a light guide comprising an optical fiber, and additionally includes signal lines to transmit the video signal and the like, a gas and liquid supply channel comprising a tube (a gas-supply liquid-supply channel) and a discharge channel. The connector 15 connected to an endoscope apparatus 7 side of the universal cable 14 branches to the signal lines, the tubes and the light guide, and are connected to respective devices. In the endoscope operating section 3, there are disposed a bending portion 16 to bend the bendable portion 5 in mutually orthogonal directions, e.g., upward-downward and right-left directions to an inserting direction, a gas-supply water-supply button 17a, a suction operating button 17b, and an after-mentioned raising base operating lever 31. Between the proximal end side of the inserting portion 4 and the endoscope operating section 3, there is disposed an inserting port 18 of a forceps channel extending from a channel opening 6a through the inserting portion 4.

The distal end portion 6 of the endoscope main body 1 is made of a hard material and formed into a cylindrical shape, and as shown in FIG. 3A, a part of a peripheral surface of the distal end portion is cut from a distal end, a part of the cut distal end portion has a flat surface 41 and the remaining part of the distal end portion is opened as the channel opening 6a. In the flat surface 41, there are disposed an illuminating window 42 to emit the illuminating light, an observing window 43 to observe the observation object region, and a nozzle 44 to jet a fluid. The illuminating window 42 is constituted of an optical lens, and irradiates the observation object region with the illuminating light guided from the light source device 8 through the optical fiber. The observation image that has passed the observing window 43 may be guided to an imaging element (not shown) disposed in the endoscope operating section 3 through the optical fiber or the like, or the image is formed by an imaging element (not shown) disposed under the observing window 43 (an objective lens) in the distal end portion 6. The imaging element is disposed integrally with an image processing circuit board by use of, for example, a CCD, a CMOS or the like, to generate the video signal from the observation image by photoelectric conversion, thereby outputting the video signal to the video processor 9.

The nozzle 44 sprays a single fluid such as a gas (air or the like) or a liquid (the stored water of the bottle 12, or the like) or a mixed fluid of the gas and the liquid so that the fluid abuts on the surfaces of the illuminating window 42 and the observing window 43, to remove dirt from the respective windows. In this operation, the gas-supply water-supply button 17a is pressed downward, whereby the gas and the liquid are selectively jetted from the nozzle 44. In addition, when the suction operating button 17b is pressed downward, an unshown pump is driven to exert suction force from the channel opening 6a of the distal end portion 6 through a treatment tool inserting channel extending through the inserting portion 4, thereby sucking and collecting an unnecessary fluid and the like from the body cavity.

A raising base unit 20 will be described with reference to FIG. 2 and FIG. 3A to FIG. 3C.

The raising base unit 20 is roughly constituted of a raising base operating mechanism 30, a raising tube path member (or a raising tube path) 25, a guide tube 23, and a raising base 21. The raising base operating mechanism 30 is housed in the endoscope operating section 3 on the proximal end side of the endoscope main body 1, and the raising base 21 is disposed in the channel opening 6a opened in the distal end portion 6. The guide tube 23 is inserted and fitted into the distal end portion 6 from the proximal end side of the endoscope inserting portion 4, and in the tube, a raising wire 24 coupling the raising base operating mechanism 30 with the raising base 21 is disposed. The raising base 21 is revolvably disposed in the channel opening 6a opened in the distal end portion 6.

In the raising base 21, as shown in FIG. 2 and FIG. 3C, a surface 21a has a dented shape, and is easily engaged with a treatment tool such as the guide wire to be bent. In the raising base 21, a revolution support point 22 is supported by a support member formed in a bottom portion of the channel opening 6a, and one end of the raising wire 24 is coupled with about a middle of the raising base 21. The other end of the raising wire 24 is coupled with the raising tube path 25 comprising an after-mentioned sealability acquiring mechanism having water tightness (or air tightness).

The raising tube path 25 is constituted of a wire fixing portion (a wire stopper) 27 coupled with the other end of the raising wire (a pulling member) 24, made of a metal material or the like and having a bar shape, and a cylindrical outer peripheral member 26 that covers the wire fixing portion 27. It is to be noted that the material of the wire fixing portion 27 is not limited to the metal material as long as the material has a rigidity equivalent to that of the metal material, and the wire fixing portion may be made of another material such as a hard resin. To couple the raising wire 24 with the wire fixing portion 27, the raising wire may be connected to the wire fixing portion by an adhesive, and when the wire fixing portion 27 is made of a metal, the raising wire 24 may be fixed to the wire fixing portion by soldering, squeezing, or caulking. There is not any special restriction on a sectional shape of the wire fixing portion 27, but the shape is preferably round.

The raising base operating mechanism 30 is constituted of a link member (a link mechanism) 28, and the raising lever 31 revolvably supported in the endoscope operating section 3 so that a knob is exposed to the outside.

In the outer peripheral member 26 and the wire fixing portion 27 in the outer peripheral member 26, the after-mentioned sealability acquiring mechanism having the water tightness or the air tightness according to each of after-mentioned embodiments is disposed. One end of the link member 28 is attached to the proximal end side of the wire fixing portion 27 extended from the outer peripheral member 26. In addition, on the proximal end side of the outer peripheral member 26, a washing opening 26a is opened into which the washing liquid flows from an oblique direction, and a washing tube 32 is connected to the washing opening. Additionally, in a case member of the endoscope operating section 3, a washing die 32a is disposed to attachably/detachably couple the washing tube 32 with an external washing liquid supply tube (not shown).

In the raising lever 31, a projecting portion 29a is disposed to revolvably support the other end of the link member 28. The link member 28 links the raising lever 31 to the wire fixing portion 27 to constitute the link mechanism, and in accordance with a lever operation of the raising lever 31, the wire fixing portion 27 moves in an advancing/retreating (forward-backward) direction along a longitudinal axis direction of the inserting portion. That is, when the wire fixing portion 27 is moved, the raising wire 24 integrally moves to revolve the raising base 21.

As shown in FIG. 3B, the treatment tool (e.g., a guide wire 40) inserted from the inserting port 18 of the forceps channel extends from the channel opening 6a, and the guide wire 40 passes a portion on the surface 21a of the raising base 21. In this case, when the raising lever 31 is operated to pull the raising wire 24, the raising base 21 revolves around the revolution support point 22 so that the raising base 21 is raised as shown by a dotted line in FIG. 2. In this case, the raising base 21 is raised in a state where the guide wire 40 is guided by a dented bottom portion of the surface 21a, to bend the guide wire 40 as shown in FIG. 3C.

Figure 4A:
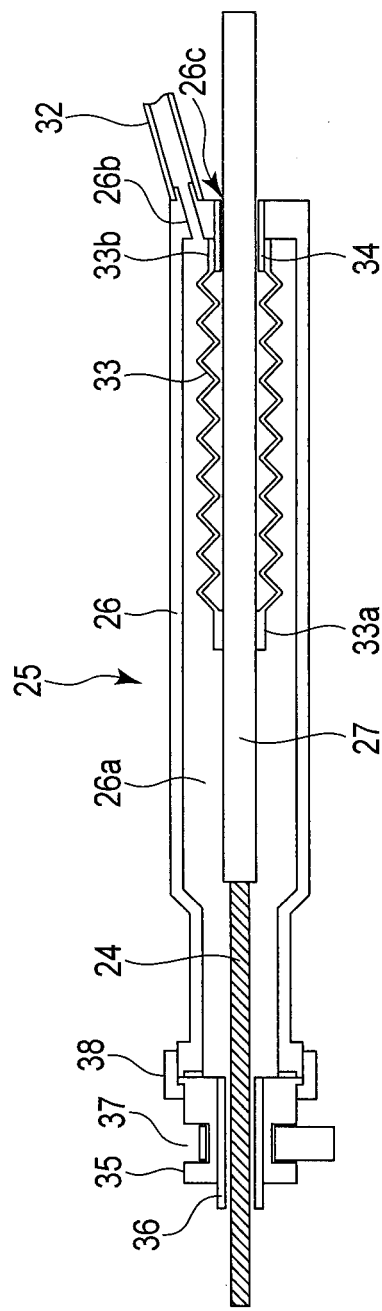
FIG. 4A is a cross-sectional view showing a constitution of a raising tube path comprising a sealability acquiring mechanism according to a first embodiment, and a state when a raising base is inverted.
Figure 4B:
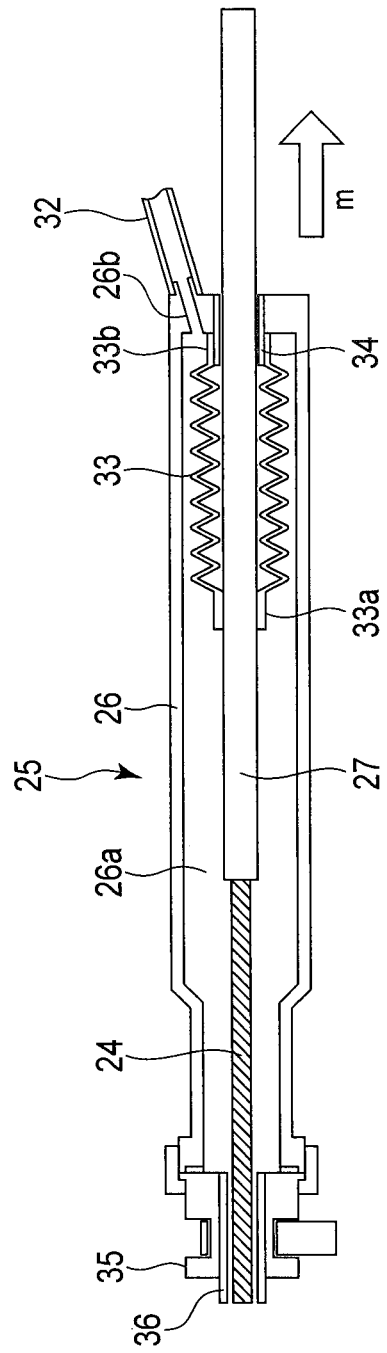
FIG. 4B is a cross-sectional view showing a state where the raising base is raised.

FIG. 4A is a cross-sectional view showing a constitution of the raising tube path comprising the sealability acquiring mechanism according to the first embodiment, and a state when the raising base is inverted, and FIG. 4B is a cross-sectional view showing a state where the raising base is raised.

In the raising tube path 25 of the present embodiment, a bottom portion (a proximal end member) is disposed at one end (on the proximal end side) of the cylindrical outer peripheral member 26, and a through hole 26c is opened in the bottom portion. Furthermore, an opening 26b for the washing liquid is formed in the oblique direction from a peripheral side of the outer peripheral member 26 toward a central side. The opening 26b for the washing liquid has a connecting die having a projected shape so that the washing tube 32 can be connected to the opening.

On the surface of the through hole 26c, a cylindrical seal fixing member 34 is disposed, and a clearance is interposed between an inner portion of the seal fixing member 34 and the wire fixing portion 27. Consequently, in the seal fixing member 34, the wire fixing portion 27 is movable with a small sliding resistance. Furthermore, an outer portion of the raising tube path 25 communicates with an inner portion of a sealing member 33 via the clearance, and air can flow outside and inside. Therefore, even when the raising wire 24 is pulled to contract the sealing member 33, a pressure of the inner portion of the sealing member 33 does not change, and the sealing member 33 does not swell. In addition, a contrivance may be made to form, for example, fine concave/convex portions on the surface of the seal fixing member 34, so that the seal fixing member comes in contact with an outer peripheral surface of the wire fixing portion 27 at points. Needless to say, this abutment portion is spatially separated from the body cavity by the after-mentioned sealing member 33, and hence, a lubricant such as a grease may be utilized.

In the inner area 26a of the outer peripheral member 26, a connecting portion between the wire fixing portion 27 and the raising wire 24 is housed, and the raising wire 24 extends from the distal end side. On the distal end side of the raising tube path 25, there are disposed a pipe 36 through which the raising wire 24 is extended to be supported, and a tube path distal end portion 35 into which the pipe 36 is fitted. The tube path distal end portion 35 is fixed to the distal end side of the outer peripheral member 26 by a ring-shaped fixing member 38.

Furthermore, the raising tube path is fixed to the inside of the endoscope operating section 3 by a fixing member 37 fitted into a concave portion disposed in the tube path distal end portion 35. According to this constitution of the raising tube path 25, the raising wire 24 and the wire fixing portion 27 are integrally movable in the outer peripheral member 26.

Furthermore, on the outer peripheral surface of the wire fixing portion 27 and an outer peripheral surface of the seal fixing member 34, the sealing member 33, whose both ends 33a and 33b are water-tightly and air-tightly bonded to the surfaces and which has bellows-shaped pleats, are disposed to cover the wire fixing portion 27. The sealing member 33 is made of, for example, an elastic material such as a rubber, a synthetic rubber or a resin, or a thin metal material, and as to a thickness and a strength of the sealing member, the thickness is preferably as small as possible and an elastic force is preferably small as long as permeation or penetration of the liquid or the gas does not occur and damages such as breaks due to expansion and contraction are not generated.

In the present embodiment, when the raising base 21 is not raised as shown in FIG. 4A (an inverted state: FIG. 3B), the raising wire 24 is not pulled by the raising lever 31, and the sealing member 33 has a natural length. In FIG. 4B, the raising lever 31 is operated to pull the raising wire 24, and as compared with FIG. 4A, the wire fixing portion 27 moves in a direction m to contract the sealing member 33.

In addition, when the sealing member 33 has the natural length, the washing liquid or the gas flows into the opening 26b from the washing tube 32 in the oblique direction, whereby the fluid flows in various directions crossing the longitudinal axis direction of the outer peripheral member 26. Therefore, the flow of the washing liquid and the gas start washing from an end portion of the sealing member 33 to which the seal fixing member 34 is applied, to also enter into bottom surfaces of extended pleats, and wash off the dirt or blow and fly the dirt to reach the tube path distal end portion 35. Furthermore, the fluid including the dirt flows through the pipe 36 of the tube path distal end portion 35, flows outside to be transferred into the forceps channel, and is discharged from the channel opening 6a to the outside.

It is to be noted that the present embodiment is a constitutional example where the sealing member 33 has the natural length when the raising base 21 is not raised (is inverted), but the present invention is not limited to this example, and may have a constitution where the sealing member 33 is contracted when the raising base is inverted. In a case where the sealing member 33 is attached to be contracted when the raising base 21 is inverted, the elastic force is always applied in a direction in which the raising base 21 is inverted. Therefore, even during the moving or during the washing, the raising base 21 holds its pressed state in the channel opening 6a, and does not rattle or does not project to the outside, so that the present embodiment has the advantage that damages due to vibrations and collision with another apparatus can be prevented.

As described above, according to the present embodiment, when the raising lever 31 is operated, less sliding resistance is applied to the wire fixing portion 27, the raising lever 31 can be operated with a lighter load (a smaller operating force amount), and the raising lever can more easily be operated when a raising angle of the treatment tool is finely regulated, as compared with a conventional mechanism in which the water tightness is realized by an O-ring.

During the washing, the fluid (the washing liquid, the gas or the like) flows into the outer peripheral member 26, and hence, when an inner pressure increases, the sealing member 33 is deformed toward an inner diameter side, i.e., toward a wire fixing portion 27 side, but by presence of the wire fixing portion 27, the sealing member is not noticeably deformed and is inhibited from being damaged.

The opening 26b to which the washing tube 32 is to be connected is disposed on the proximal end side of the outer peripheral member 26, and hence, irrespective of the operation of the wire fixing portion 27 or the link mechanism, the washing tube 32 is fixed in an immobile state, and deterioration, looseness or removal of the washing tube 32 is prevented. Furthermore, the washing fluid flows from the oblique direction into the outer peripheral member 26, and hence, the washing liquid or the gas is spread in the whole outer peripheral member 26, so that the washing can suitably be realized.

When the raising base 21 is inverted, the sealing member 33 has the natural length, and hence, the loads to be applied to the sealing member 33 are decreased, and a product life advantageously is not shortened. In addition, also when the endoscope main body is stored, the raising base 21 is inverted, and hence, the loads to be applied to the sealing member 33 during the storage are decreased. It is to be noted that, when the sealing member 33 does not have the natural length but is elongated and attached, a stroke of the sealing member 33 can be lengthened due to the elongation. That is, the stroke in a case where the sealing member is elongated from the natural length is added to a stroke in a case where the sealing member can be contracted from the natural length, and hence, even the same sealing member can take a longer stroke. In addition, the required stroke can be obtained from the shorter sealing member, and hence, the total length of the sealing member can be shortened.

Figure 5A:
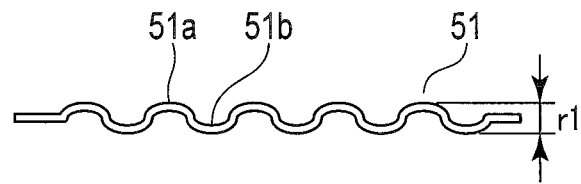
FIG. 5A is a view showing a cross-sectional constitution of a part of a sealing member of a sealability acquiring mechanism according to a first modification of the first embodiment.
Figure 5B:
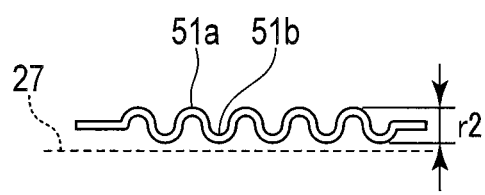
FIG. 5B is a view showing a cross-sectional constitution of a part of the sealing member of the sealability acquiring mechanism according to the first modification of the first embodiment.

Next, FIGS. 5A and 5B are views showing a cross-sectional constitution of a part of a sealing member of a sealability acquiring mechanism according to a first modification of the first embodiment. In this example, FIG. 5A shows a state of the sealing member when a raising base is inverted, and FIG. 5B shows a state of the sealing member when the raising base is raised.

As shown in FIG. 5A, in the first embodiment, the sealing member 33 has a bellows shape obtained by alternately disposing flat surfaces and folds, but in the present modification, there is provided a sealing member 51 having a wave type shape obtained by a combination of circular portions 51a and 51b in which corner portions are rounded.

FIG. 5A shows the state of the sealing member 51 having a natural length when the raising base is inverted in the same manner as in FIG. 4A. In addition, FIG. 5B shows a state of the contracted sealing member 51 when the raising base is raised in the same manner as in FIG. 4B. At this time, in a case where the sealing member 51 of the natural length has an amplitude r1, the sealing member is contracted to have an amplitude r2 higher than the amplitude r1, but each apex (mountain) 51a is circularly contracted and has a state where a clearance is generated between pleats.

According to the present modification, when the wave-type shaped sealing member 51 is contracted, a portion between the pleats is not closed and the clearance is circularly made, and hence, when washing is performed, a washing liquid or a gas is entirely spread also in pleat inner portions 51b, and substances adhering to the pleat inner portions 51b can easily be removed. In addition, there are not any bent folds, and hence, the sealing member has a further durability against elongation and contraction.

Figure 6A:
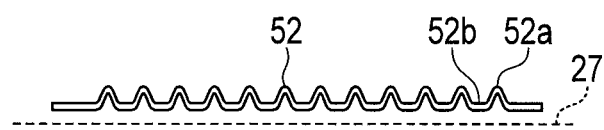
FIG. 6A is a view showing a cross-sectional constitution of a part of a sealing member of a sealability acquiring mechanism according to a second modification of the first embodiment.
Figure 6B:
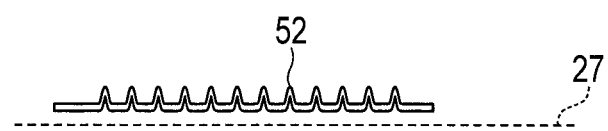
FIG. 6B is a view showing a cross-sectional constitution of the part of the sealing member of the sealability acquiring mechanism according to the second modification of the first embodiment.

Next, FIGS. 6A and 6B are views showing a cross-sectional constitution of a part of a sealing member of a sealability acquiring mechanism according to a second modification of the first embodiment. In this example, FIG. 6A shows a state of the sealing member when a raising base is inverted, and FIG. 6B shows a state of the sealing member when the raising base is raised.

In the present modification, there is provided a sealing member 52 having a wave type shape obtained by alternately combining circular mountain portions 52a in which corner portions are rounded and flat valley portions 52b. In the present modification, in a case where the sealing member is contracted as shown in FIG. 6B, an interval between the valley portions 52b is not changed but is maintained even when foot portions of the mountain portions 52a are narrowed.

According to the present modification, the flat valley portion 52b is present between the mountain portions 52a, and hence, when the sealing member is contracted, a portion between pleats is not closed and a flat clearance is made, and when washing is performed, a washing liquid or a gas is entirely spread also in bottom portions of the pleats, and substances adhering to inner portions of the pleats can easily be removed.

Next, FIG. 7 is a view showing an appearance constitution of a sealing member of a sealability acquiring mechanism according to a third modification of the first embodiment. It is to be noted that constitutional regions other than a sealing member 53 are equivalent to those of the abovementioned first embodiment and their descriptions are omitted herein.

The present modification has a constitution where mountain portions of bellows of the sealing member 53 are continuously spirally formed on a periphery of a wire fixing portion 27. The sealing member 53 is made of a material equivalent to the abovementioned material of the sealing member 33. Both ends 53a and 53b of the sealing member 53 are bonded and fixed so that a rear end member 54 is watertight. In addition, although not shown in FIG. 7, an opening 26b for a washing liquid is formed as shown in FIG. 4A. In this modification, the opening 26b for the washing liquid is opened in an oblique direction from a peripheral side of an outer peripheral member 26 toward a central side in the same manner as in the first embodiment, and additionally, as to an opening direction of the opening 26b for the washing liquid, the opening is opened in the same spiral direction so that a fluid such as the washing liquid flows along the spiral shape of the sealing member 53. It is to be noted that also in the abovementioned first embodiment, the opening 26b for the washing liquid may be opened in a spiral direction so that the fluid flows in a spiral manner in the same manner as in the present modification.

Next, FIG. 8A is a cross-sectional view showing a constitution of a raising tube path comprising a sealability acquiring mechanism according to a second embodiment, and a state when a raising base is inverted, and FIG. 8B is a cross-sectional view showing a state when the raising base is raised. In constitutional regions of the present embodiment, the constitutional regions equivalent to those of the abovementioned first embodiment are denoted with the same reference signs and their descriptions are omitted.

In a raising tube path 60 of the present embodiment, one end (a proximal end side) of a cylindrical outer peripheral member 61 is formed as an opening end that is straightly opened, and at the other end (on a distal end side), there are disposed a pipe 36 through which a raising wire 24 is extended to be movably supported, and a tube path distal end portion 35 into which the pipe 36 is fitted. The tube path distal end portion 35 is fixed to a distal end side of an outer peripheral member 26 by a ring-shaped fixing member 38. The pipe 36 may have a constitution where fine concave/convex portions are formed on an inner surface to decrease loads due to friction with the raising wire 24, whereby the pipe comes in contact with the raising wire 24 at points.

Into the one end (the proximal end side) of the outer peripheral member 61, one end (an opening end) of a cylindrical sealing member 63 made of an elastic material and forming the same shape as in a sectional shape of the opening end of the outer peripheral member is fitted to come in contact closely with the one end of the outer peripheral member, and is fixed by a fixing member 64 made of a liner material. In addition, the other end (an opening end) of the sealing member 63 is fitted into an outer peripheral surface of a rear end member (a connecting member) 62 and fixed by the fixing member 64. The rear end member 62 is made of a hard material such as a metal or a hard resin, and is water-tightly (or air-tightly) fixed by extending a wire fixing portion 27 through a through hole 62b in the center of the rear end member.

Additionally, in the same manner as in the first embodiment, there is disposed an opening 62a for a washing liquid which is to introduce a gas (e.g., air) and a liquid (e.g., washing water) into an inner space 65 of the outer peripheral member 26. An unshown washing tube is attached to a die portion of the opening 62a for the washing liquid. In the inner space 65 of the outer peripheral member 61, the wire fixing portion 27 is connected to the raising wire 24 inserted from the pipe 36. Therefore, the inner space 65 of the outer peripheral member 26 is separated from an outer space (a space in an operating section 3) by the sealing member 63, and hence, the liquid or the like does not leak from the outer peripheral member 26 into the operating section 3.

In this constitution, as shown in FIG. 8B, an unshown raising lever 31 is operated to pull and move the wire fixing portion 27 in a direction m, and the sealing member 63 is stretched in a direction P. In this case, the sealing member 63 is made of a material weak in elastic force, and hence, it is possible to decrease loads when the lever is operated.

In this constitution, as shown in FIG. 8A, a raising base (see FIG. 2) disposed on the distal end side is inverted, and the sealing member 63 is attached to have a natural length.

According to the abovementioned present embodiment, during storage, i.e., when the raising base is inverted, the sealing member 63 has the natural length, and hence, the loads to be applied to the sealing member 63 are decreased. Furthermore, when the raising lever 31 is operated to pull the wire fixing portion 27 and the sealing member 63 is stretched, the sealing member does not swell outward more than its original diameter. In consequence, even when another component is disposed at a position close to the sealing member 63, the component does not come in contact with the sealing member but can compactly be disposed. In addition, the sealing member 63 is attached to a position at which a raising tube is exposed, and hence, the sealing member does not interfere with the other component but can easily be replaced alone.

Figure 11A:
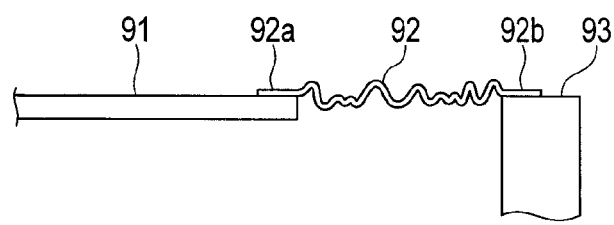
FIG. 11A is a view showing a constitutional example of a sealing member according to a modification of the second embodiment.
Figure 11B:
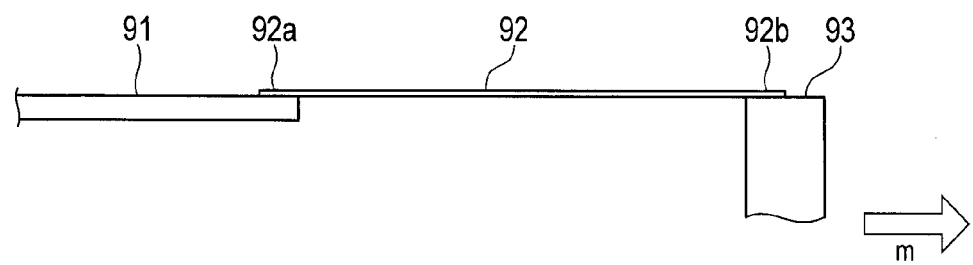
FIG. 11B is a view showing a constitutional example of the sealing member according to the modification of the second embodiment.

In addition, as a modification of the second embodiment, a sealing member 92 may be attached to be bent' when a raising base is inverted as shown in FIG. 11A. By an operation of the raising lever 31 shown in FIG. 2, as shown in FIG. 11B, a rear end member 93 is pulled in a direction m by a wire fixing portion to stretch the sealing member 92, and in this case, the sealing member does not swell outward more than its original diameter. The sealing member 92 may be an elastic member but may also be a thin resin film.

According to the present modification, during storage, i.e., when the raising base is inverted, the bent sealing member 92 is fixed between an outer peripheral member 91 and the rear end member 93, and in this case, during non-use or during the storage, loads to be applied to the sealing member 92 can be decreased, and further, a total length of a raising tube path 25 can be shortened to achieve space saving.

Figure 9A:
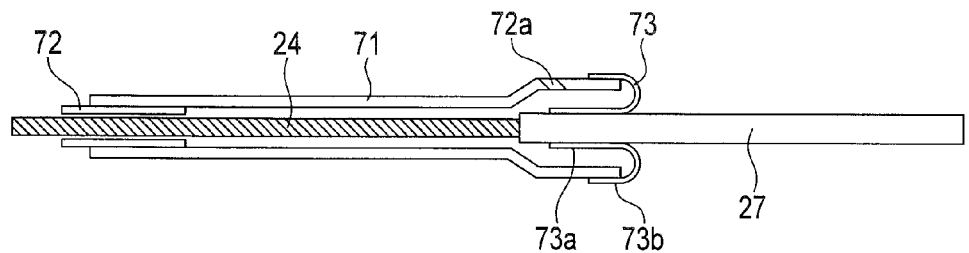
FIG. 9A is a cross-sectional view showing a constitution of a raising tube path comprising a sealability acquiring mechanism according to a third embodiment, and a state when the raising base is inverted.
Figure 9B:
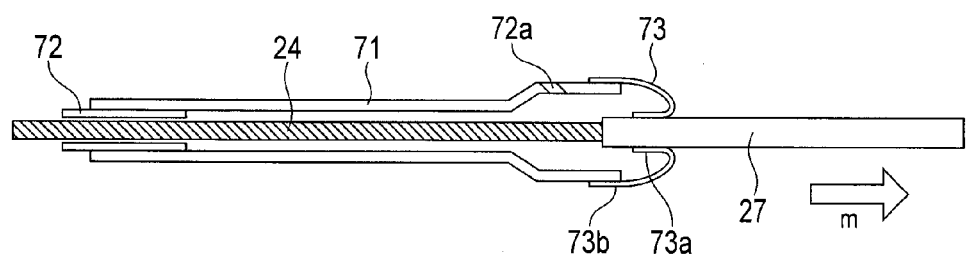
FIG. 9B is a cross-sectional view showing a state when the raising base is raised.

Next, FIG. 9A is a cross-sectional view showing a constitution of a raising tube path comprising a sealability acquiring mechanism according to a third embodiment, and a state where a raising base is inverted, and FIG. 9B is a cross-sectional view showing a state when the raising base is raised. In constitutional regions of the present embodiment, the constitutional regions equivalent to those of the abovementioned first embodiment are denoted with the same reference signs and their descriptions are omitted.

As shown in FIG. 9A, the raising tube path of the present embodiment is constituted of a cylindrical outer peripheral member 71 having a stepped portion due to different diameters, a raising wire 24 and a wire fixing portion 27 extending through the outer peripheral member 71 to be movably disposed, a sealing member 73 fixed to be applied to the outer peripheral member 71 and the wire fixing portion 27, and a pipe 72 which is disposed on a small diameter side (a distal end side) of the outer peripheral member. 71 and through which the raising wire 24 extends.

The outer peripheral member 71 is made of a metal, a hard resin or the like, and has a cylindrical shape in which two large and small cylinders having different diameters are integrally formed by disposing the stepped portion. On a large diameter side (a proximal end side) of the outer peripheral member 71, a through hole 72a is opened in an oblique direction from an outer peripheral surface toward the proximal end side (an opening side). The through hole 72a is provided with the abovementioned die to be utilized as an opening for a washing liquid.

The sealing member 73 is inserted from one end 73a side into the wire fixing portion 27 and fixed to the wire fixing portion 27 water-tightly (or air-tightly) by an adhesive or the like. The other end (an inside-out fixing portion) 73b of the sealing member 73 is returned and expanded to cover a large-diameter outer peripheral surface (the proximal end side) of the outer peripheral member 71, and bonded to be water-tightly (or air-tightly) fixed (fixed inside out). The sealing member may be fixed by a fixing member made of a linear material in the same manner as in the abovementioned second embodiment.

According to such a constitution, the sealing member 73 is interposed between the wire fixing portion 27 and the outer peripheral member 71 to close a portion therebetween, and separates an inner space of the outer peripheral member 71 from an outer space of the outer peripheral member 71 (an inner portion of an operating section 3). The sealing member 73 is made of, for example, an elastic material such as a rubber, a synthetic rubber or a resin, or a thin metal material, and as to a thickness and a strength of the sealing member, the thickness is preferably as small as possible and an elastic force is preferably small in a range where permeation or penetration of a liquid or a gas does not occur and damages such as breaks due to bending are not generated.

As shown in FIG. 9B, the wire fixing portion 27 is pulled in a direction m by an operation of an unshown raising lever (see FIG. 2), whereby the sealing member 73 is pulled to the outside in the same manner as in a roller.

According to the present embodiment, an amount of the sealing member 73 to be expanded or contracted is small, and hence, loads to be applied to the sealing member 73 can be decreased, and product characteristics can be maintained long. When the wire fixing portion 27 is pulled, the sealing member 73 functions without being expanded in an outer peripheral direction, and hence, another component can be disposed around the sealing member 73, which can contribute to compactness of the operating section. The sealability acquiring mechanism of the present embodiment has a simpler structure and a smaller number of components, and can therefore be realized inexpensively.

Figure 10A:
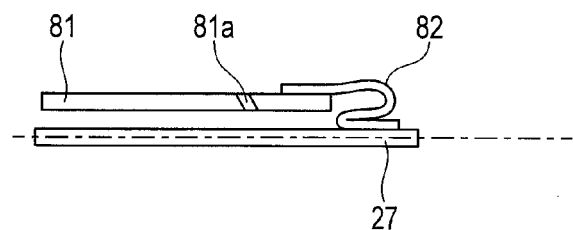
FIG. 10A is a view showing a partial cross-sectional constitution of a sealing member of a sealability acquiring mechanism according to a first modification of the third embodiment.
Figure 10B:
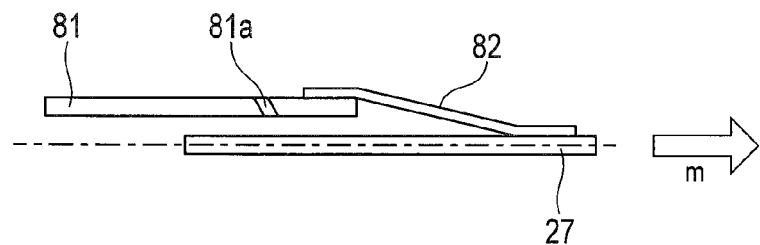
FIG. 10B is a view showing a partial cross-sectional constitution of the sealing member of the sealability acquiring mechanism according to the first modification of the third embodiment.

Next, FIGS. 10A and 10B are views of a partial cross-sectional constitution of a sealing member of a sealability acquiring mechanism according to a first modification of the third embodiment. FIG. 10A is a cross-sectional view showing a state of the sealing member when a raising base is inverted, and FIG. 10B is a cross-sectional view showing a state of the sealing member when the raising base is raised.

As shown in FIG. 10A, a sealing member 82 is water-tightly (or air-tightly) fixed by bonding one end of the sealing member to an outer peripheral surface of an outer peripheral member 81, a bent portion is formed and folded up, and the other end of the sealing member is similarly bonded to a wire fixing portion 27 disposed in the outer peripheral member 81. In the outer peripheral member 81, a through hole 81a to be utilized as an opening for a washing liquid is opened in an oblique direction from the outer peripheral surface toward a proximal end side (an opening side).

Additionally, as shown in FIG. 10B, the wire fixing portion 27 is pulled in a direction m by an operation of an unshown raising lever (see FIG. 2), whereby the folded-up sealing member 82 extends to be applied from the outer peripheral member 81 to the wire fixing portion 27 and expands in a tapered shape. The sealing member 82 is made of an elastic material in a constitution where the sealing member is stretched when extending, and the sealing member may be made of a thin resin film in a constitution where the sealing member is not stretched.

Additionally, in the sealing member 82, a thickness of the bent portion may be smaller than that of another portion so that the sealing member is easily folded up, and hence, the sealing member can easily be bent and folded in the same shape. A shape change of the sealing member 82 in accordance with the movement of the wire fixing portion 27 is performed without being expanded in an outer peripheral direction, and hence, another component can be disposed around the sealing member 82, which can contribute to compactness of the operating section.

Next, modifications according to the second and third embodiments will be described. In these examples, a shape change of a sealing member is performed without being expanded in an outer peripheral direction, but in this modification, a guide is further disposed to more stably realize the shape change of the sealing member.

FIG. 12A shows a constitution where a coiled spring guide (an annular rough line) 101 is fitted into an outer side of a sealing member 102 (reference sign 63 of FIG. 8A) having the abovementioned cylindrical shape shown in FIG. 8A. FIG. 12B shows that the sealing member 102 is attached so that the sealing member 102 is bent as shown in FIG. 11A when an unshown raising base is inverted. FIG. 12C shows that the sealing member 102 is pulled to be stretched by an unshown wire fixing portion.

As shown in FIG. 12C, when the sealing member 102 is bent, the sealing member is restricted by the spring guide 101 so that a bent portion does not expand to an outer peripheral portion.

According to the present modification, when the stored apparatus is taken outside or when the apparatus is conveyed in a state where the raising base is inverted, even the bent sealing member 102 does not come in contact with any constitutional regions disposed around the sealing member, and the sealing member can be prevented from being damaged. In addition, when the shape change of the sealing member 102 is performed, an outer diameter is prevented from being noticeably changed, and hence, another component can be disposed around the sealing member 102, which can contribute to compactness of an operating section.

According to the present invention, there can be provided a medical apparatus which does not disturb operating properties but securely realizes water tightness or air tightness.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:

1. A medical apparatus having:
   a revolvable raising base disposed in a distal end portion of an inserting portion to be inserted into a body cavity;
   a pulling member that revolves the raising base with a pulling force imparted by a raising base operating mechanism;
   a tube path member comprising an outer peripheral member and a pulling member fixing portion coupled with the pulling member, the pulling member fixing portion coupled with the pulling member being inserted into the outer peripheral member;
   a sealing member that is fixed to each of the pulling member fixing portion and the outer peripheral member, is deformable in accordance with movement of the pulling member, and water-tightly or air-tightly separates an inner portion of the outer peripheral member from an outer portion of the pulling member fixing portion; and
   an opening to supply a fluid flowing in the outer peripheral member,
   wherein the sealing member is water-tightly or air-tightly fixed to an outer peripheral surface of the pulling member fixing portion to be disposed in the outer peripheral member so that the fluid supplied through the opening flows between an inner peripheral surface of the outer peripheral member and an outer peripheral surface of the sealing member.

2. The medical apparatus according to claim 1, which has:
   a proximal end member which is disposed on a proximal end side of the tube path member and in which a through hole is opened into which the pulling member is inserted; and
   a seal fixing portion which is disposed around the through hole of the proximal end member and into which the sealing member is fitted to be water-tightly or air-tightly fixed.

3. The medical apparatus according to claim 1, which has:
   a connecting member to be attached to the pulling member; and
   an opening disposed in the connecting member to supply a fluid flowing in the tube path member,
   wherein a proximal end side of the sealing member is water-tightly or air-tightly fixed to the connecting member, and a distal end side of the sealing member is water-tightly or air-tightly fixed to the tube path member.

4. The medical apparatus according to claim 1, wherein the sealing member has an inside-out fixing portion whose outer peripheral surface is water-tightly or air-tightly fixed to the whole outer periphery of the pulling member.

5. The medical apparatus according to claim 1, wherein the sealing member is made of an elastic material.

6. The medical apparatus according to claim 5, wherein on an outer periphery of the sealing member, there is fitted a coil that restricts the sealing member from being expanded on an outer peripheral portion side when the sealing member is bent.

7. The medical apparatus according to claim 1, wherein the sealing member is formed in a bellows shape.

8. The medical apparatus according to claim 1, wherein the sealing member is formed into a cylindrical shape, and a distal end side and a proximal end side of the sealing member are water-tightly or air-tightly fixed to the pulling member and the tube path member, respectively.

9. The medical apparatus according to claim 1, wherein the raising base operating mechanism includes a link mechanism that imparts the pulling force to the pulling member in accordance with an operation of revolving a supported lever.

10. The medical apparatus according to claim 1,
    wherein the pulling member is connected to a wire fixing portion coupled with the raising base operating mechanism and having a bar shape, and
    a proximal end side of the sealing member is water-tightly or air-tightly fixed to the wire fixing portion, and a distal end side of the sealing member is water-tightly or air-tightly fixed to the tube path member.

* * * * *